United States Patent [19]

Lewis et al.

[11] Patent Number: 4,637,992

[45] Date of Patent: Jan. 20, 1987

[54] INTERCALATED CLAY COMPOSITIONS

[75] Inventors: Robert M. Lewis, Sugarland, Tex.; Rutger A. Van Santen, Amsterdam, Netherlands

[73] Assignee: Shell Oil Company, Houston, Tex.

[21] Appl. No.: 682,732

[22] Filed: Dec. 17, 1984

[51] Int. Cl.⁴ .............................................. B01J 21/16
[52] U.S. Cl. ....................................................... 502/84
[58] Field of Search ...................................... 502/80, 84

[56] References Cited

U.S. PATENT DOCUMENTS 4,410,751 10/1983 Shin et al. ......................... 502/84 X
4,510,257 4/1985 Lewis et al. ...................... 502/84 X
4,515,901 5/1985 Elattar .............................. 502/84 X Primary Examiner—Carl F. Dees

[57] ABSTRACT

This invention relates to clay compositions intercalated with inorganic oxide particles and the process from preparing them.

7 Claims, 2 Drawing Figures

INTERCALATED CLAY COMPOSITIONS

FIELD OF THE INVENTION

The present invention relates to clay compositions wherein the layers of said clay have been intercalated with colloidal inorganic oxide particles. These materials have useful catalytic and adsorbent properties.

BACKGROUND OF THE INVENTION

Layered naturally occurring and synthetic smectites such as bentonite, montmorillonites and chlorites may be visualized as a "sandwich" composed of two outer layers of silicon tetrahedra and an inner layer of alumina octahedra. These "sandwiches" or platelets are stacked one upon the other to yield a clay particle. Normally this arrangement yields a repeated structure about every nine and one-half angstroms. A considerable amount of study has shown that these platelets can be separated further, by as much as 30 to 40 Å, i.e. interlayered by intercalation of various polar molecules such as water, ethylene glycol, and various amines. The solvent interlayered clays thus far prepared from naturally occurring smectites, however, are not suitable for general adsorbent and catalytic applications because they tend to collapse when subjected to high temperature.

In the past, clay materials have been intercalated with a variety of materials in order to form a supported open structure material which is useful as an adsorbent, a catalyst support, filtration medium or the like. However, it has been difficult to obtain a modified clay material which is stable at relatively high temperatures on the order of 250° C.–500° C. When a solvent swollen clay is heated to high temperature, the solvent is vaporized and collapse of the silicate sheets of the clay results as the solvent is removed from the interlamellar regions. This collapse significantly reduces the surface area of the clay because the internal surfaces are no longer available for adsorption. To solve this problem, a number of approaches have been taken to modify the clay by introducing supports or "columns" of material into the interlamellar regions of the clay to hold the silicate sheets of the clay apart. For instance, in the preparation of clay materials intended for use at relatively low to moderate temperatures, the clay layers have been separated with an organic material. For instance Shabtai et al. Proc. 6th Int. Congr. Catal., B5, 1-7 (1976) show a system in which smectite is interacted with di-or polycations derived from rigid, preferably cage-like amines, which acquire a single stable orientation in the interlayer space because of the steric requirements dictated by the configuration of the structure. A 1,4-diazabicyclo[2.2.2]octane-montmorillonite was found to possess significant molecular sieve properties and markedly higher catalytic activity for esterification of carboxylic acids in comparison to ordinary alkylammonium-exchanged montmorillonites.

The kaolin group materials comprise a silica tetrahedral sheet and an alumina octahedral sheet combined into the kaolin unit layer. Seto et al U.S. Pat. No. 4,159,994 show the intercalation of kaolin materials with an ammonium salt of a carboxylic acid having more than two carbon atoms, the alkali metal salt of a carboxylic acid having more than two carbon atoms, a lower alkylene glycol or a quaternized ammonium radical.

Because of the failure of the organic material impregnated clays at high temperatures, approaches have been taken to improve the stability of intercalated clays at high temperatures by intercalating clay substrates with various inorganic compounds, such as, for example, compounds of aluminum, bismuth, chromium, nickel, niobium, magnesium, silicon, tantalum and zirconium. Early work was carried out using aluminum chlorhydroxide as a pillaring agent. For example, see U.S. Pat. No. 4,176,090 issued Nov. 27, 1979 to Vaughan et al. Shabtai (U.S. Pat. No. 4,216,188 issued Aug. 5, 1980) uses colloidal solutions of metal hydroxides (sols) dispersed in the form of low molecular weight oligomers of polymers of aluminum or chromium hydroxides as pillaring agents. In Raible (U.S. Pat. No. 3,676,367 issued July 11, 1972) montmorin minerals are suspended in silicate solutions and subsequently free silica in precipitated between the layers of the montmorin mineral. More recent work has concentrated on using complexed ionic silicon as a pillaring agent. See, for example, the work of Pinnavaia et al, U.S. Pat. No. 4,376,163 issued Jan. 4, 1983.

Consistent among all the inorganic intercalated materials reported in the literature is a limited range of layer separations. Layer separation refers to the distance between facing clay surfaces on each side of the pillar ($d_1$ in FIG. 1). These materials exhibit a layer separation ranging from about 3 to about 9 angstroms. The aluminum-containing pillars are at the upper end of the range and the silicon pillars are at the lower end of the range. The instant invention extends the range of layer separation distances obtainable using inorganic pillaring materials. Large layer separation distances allow the use of higher molecular weight and bulkier organic molecules to take part in catalytic reactions and adsorption processes.

SUMMARY OF THE INVENTION

The present invention relates to clay compositions wherein the layers of said clay have been intercalated with colloidal inorganic oxide particles. The invention also relates to the process for preparing the intercalated clays which comprises contacting a swellable layer clay with a solution of colloidal inorganic oxide particles have a positive surface charge, separating the resulting intercalated clay from the solution and drying. These materials are useful as catalysts, catalyst supports and adsorbents.

DESCRIPTION OF THE PREFERRED EMBODIMENTS

The outstanding feature of the present invention is that a clay based composition is provided in which the open, porous network of the clay is stabilized by colloidal inorganic oxide particles intercalated between the layers of the clay, resulting in an layer spacing ($d_2$) of greater than the 12–16 Å which is obtained by the prior art. The term "intercalation" is a term of art which indicates the insertion of a material between the layers of a clay substrate. The article authored by Loeppert, Jr. et al, Clays and Clay Minerals, 27(3), 201–208 (1979) is an example of a reference which uses the term in the same way it is used in the present specification. As used herein the term "layer spacing" refers to the 001 spacing which is represented by the term "d$_2$" in FIGS. 1 and 2. The term "layer separation" refers to the distance between the faces of two adjacent clay layers and is represented the term "d$_1$" in FIGS. 1 and 2. The term "pillar separation" refers to the distance between adjacent pillars and is represented by the term "d$_3$" in FIG. 2.

Figure 1:
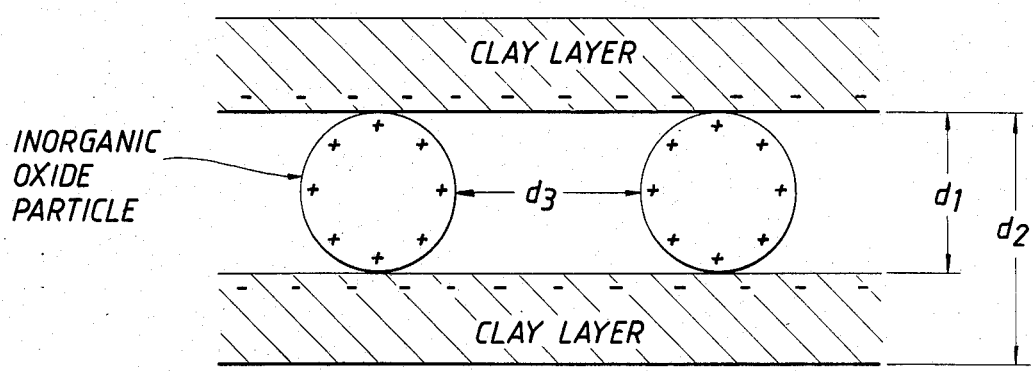
FIG. 1 is a representation of the inorganic oxide intercalated clay of the instant invention.

The clays which can be utilized as starting materials for the clay product of the invention are those lattice clay minerals and their synthetic analogues which are capable of swelling. These clays have swellable layers between which guest molecules can be intercalated. These layers typically are composed of sheets of aluminum and silicon ions. The two main structural types are where the swellable layer comprises either a two-"layered" sheet or a three-"layered" sheet. Kaolinites and kandites are illustrations of the former and the smectites and vermiculites are illustrations of the latter. In FIG. 1, the clay layers represent these two- or three- "layered" sheets and are what are referred to herein as swellable layers.

Suitable clays include the expandable smectites and vermiculite, as well as synthetic forms thereof such as reduced charge montmorillonite. Hofmann et al, Z. Anorg. Allg. Chem., 212, 995–999 (1950) and G. W. Brindley et al, Clays and Clay Minerals, 19, 399–404 (1971) describe methods of preparing such synthetic clays.

Smectites are 2:1 clay minerals that carry a lattice charge and characteristically expand when solvated with water and alcohols, most notably ethylene glycol and glycerol, and are generally represented by the formula:

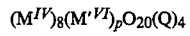

$$(M^{IV})_8(M'^{VI})_pO_{20}(Q)_4$$

wherein p equals 4 for cations with a +3 charge, equals 6 for cations with a +2 charge, Q is hydroxyl or fluoride, IV indicates an ion coordinated to four other ions, and VI indicates an ion coordinated to six other ions. M is commonly $Si^{4+}$, optionally partially substituted by other ions such as $Al^{3+}$ and/or $Fe^{3+}$ as well as several other four coordinate ions such as $P^{5+}$, $B^3$, $Ge^{4+}$, $Be^{2+}$, and the like. M' is commonly $Al^{3+}$ or $Mg^{2+}$, but also may be partially substituted with hexacoordinate ions such as $Fe^{3+}$, $Fe^{2+}$, $Ni^{2+}$, $Co^{2+}$, $Li^+$, and the like. The charge deficiencies created by the various substitutions into these four and six coordinate cation positions are balanced by one or several cations located between the structural units. Water may also be coordinated to these structural units, bonded either to the structure itself, or to the cations as a hydration shell. When dehydrated, the above structural units have a repeat distance or interlayer spacing of about 9 to 12 Å, as measured by X-ray diffraction. Commercially available smectites include montmorillonite, bentonite, beidellite, hectorite, saponite, sauconite and nontronite.

The inorganic oxides that are used to prepare the clays in the instant process are those metal and semi-metal oxides that are substantially insoluble in highly polar solvents, particularly those that are insoluble in water. These include, for example, oxides of the transition metal series; the Lanthanide series; the Actinide series; metals from Group IIA of the Periodic Table such as beryllium and magnesium; metals from Group IIIA such as, aluminum, gallium, etc; semi-metals or metals from Group VA such as, silicon, germanium, lead, etc.; and metals from Group VIA such as, selenium and telurium.

In preparing the intercalated clays of the instant invention, the clay to be intercalated is contacted with a colloidal suspension df the above-described inorganic oxides. The colloidal oxides must be substantially insoluble in the suspension medium. The suspension medium is one that is suitable for carrying out ion exchanqe with the clay. In general, the suspension medium is a highly polar solvent. Examples are water, amides, lower alcohols such as, methanol, ethanol and isopropanol and lower polyols such as, ethylene glycol. Water is the preferred medium.

The colloidal inorganic oxide particles as suspended generally are sized at less than about 200 Å, preferably less than about 100 Å, more preferably less than about 50 Å and most preferably less than about 25 Å. When the colloidal suspension contains a range of sizes for example, 10 to 200 Å, the sizes in the lower ranges, say, less than 25 Å will be preferentially intercalated into the clay. Special measures may be needed to intercalate larger sizes into the clay, such as, preswelling the clay with suitable organic solvents. It is also possible that the larger sizes will also be broken down into smaller sizes during the intercalated process, which smaller sizes preferentially intercalate between the lay laters. The lower limits on the particle sizes of the colloidal particles is determined by the size needed to maintain a colloidal suspension. Generally, the literature somewhat arbitrarily has chosen about 10 angstroms as being the lower limit to particle size in determining a colloidal suspension or "solution". The size should be large enough so that the colloidal suspension shows properties having marked deviations from the properties of a true solution. Hence, the lower limit can be somewhat higher or lower than 10 angstroms depending on the particular colloid particle or suspension medium involved. In general, the colloid size ranges from about 10 to about 200, preferably from about 20 to about 100, more preferably from about 10 to about 50 and most preferably from about 10 to about 25 angstroms.

One necessary condition for the preparation of compositions of the instant invention is that the colloidal particles in the colloid suspension have at least a slight positive surface charges. It is postulated that the need for a positive surface charge relates to ion exchange phenomena. It is thought that colloidal particles with surface charges are attached to the clay interlayers and displace positively charged alkali metal ions there, in effect, carrying out a "gross" sort of ion exchange. By the same token, no exchange would take place when the colloidal particles have a neutral or negative change.

The science of colloids is well established and methods for preparing colloids can be readily found in the literation. Colloids have found many uses in industry. They are used in paints, inks, cosmetics, pharmaceuticals, plastics, detergents, soaps, etc. Colloidal suspensions are generally divided into two main categories: lyophilic (solvent-loving) and lyophobic (solvent-hating). Generally, the method of making colloidal suspension can provide colloids with given surface charges. In many cases, particularly with lyophilic colloids, the surface can be determined by the pH of the suspension medium.

Colliodal suspensions having characteristics suitable for use in the instant invention are obtainable from commercial sources. For example, The PQ Corporation, Valley Forge, Pa., can provide colloidal suspension of particles of yttria, zirconia, chromia, ceria and alumina all carrying a slightly positive surface charge.

The general technique for preparing the intercalated clays of the instant invention comprises adding the clay in ground form to the colloidal suspension, stirring for a suitable period of time to allow intercalation, separating the clay from the suspension media by conventional techniques, such as, filtration or centrifugation, and then drying the intercalated clay. Variations of the above-generalized technique will be obvious to one skilled in the art. For example, the clay can be slurried with a suitable medium such as water, and then combined with the colloidal suspension, or the colloidal suspension can be prepared directly in the clay slurrying medium. Drying of the intercalated clays will be carried out at temperatures suitable for the particular suspending medium involved. For water, temperatures will range from about ambient, say 50° C. to about 150° C., although different temperatures may be used in combination with vacuum or forced air drying. In general, where the intercalated clay is later to be used at elevated temperature, it is stabilized by calcining. Suitable calcining temperatures range from about 100° C. to about 800° C. preferably from about 200° C. to about 600° C. The clay substrate can be swelled with a solvent compound capable of swelling the clay prior to contact with the colloidal suspension, or a solvent compound capable of swelling the clay may be added to the colloidal solution. Suitable swelling compounds are polar compounds such as water, ketones like acetone, methylethylketone, etc; sulfoxides like dimethylsulfoxide; formamides and the like. These swelling agents have been extensively studied and one skilled in the art can find many suitable ones from the literature. The swelling solvent and the solvent suspending the colloidal particles should be mutually soluble in the concentration ranges utilized.

The temperature at which the clay is impregnated with the colloidal suspension is not critical. Normally, the temperature used is about room temperature, although temperatures ranging from the freezing point to the boiling point of the solution containing the colloidal particles are satisfactory.

The clay substrate is impregnated with an amount of colloidal inorganic oxide particles sufficient to give an intercalated structure. The amount of colloidal particles intercalated within the layers should be an amount at least sufficient to maintain the spacing of the expanded clay.

In a general fashion the compositions of the instant invention which comprise clays intercalated with three-dimentional inorganic oxide particles (pillars) are prepared by contacting or impregnating the clay with a solution containing suspended therein colloidal inorganic oxide particles which particles generally have sizes less than 200 Å. At times the intercalated clays are utilized as such after removing excess solvent, say by drying with moderate heat and/or vacuum. But more frequently the intercalated clay is subsequently calcined, frequently in an oxidizing atmosphere, at temperatures ranging from about 100° C. to about 800° C., preferably from about 200°-800° C.

In general, the intercalated clays of the instant invention will have layer separations greater than that obtained using prior art technique. This layer separation will generally be greater than about 10 Å, preferably greater than 15-16 Å, and will preferably be in the ranges between about 16 and about 25 Å.

The intercalated clay product of the present invention is useful as an absorbent in a variety of applications, especially as particles in a Tyler mesh size range of 4 to 400, or in a spray dried form and can be used as a catalyst support for various catalytically active metals such as a Group VIII metal such as platinum, palladium, nickel, iron or cobalt; molybdenum; tungsten; a rare-earth metal and the like. It can also be used in the proton form, i.e., with hydrogen and ammonium ions present. Moreover, the intercalated product can be used in admixture with other common adsorbents or matrix materials such as silica, alumina, silica-alumina hydrogel, crystalline aluminosilicate zeolite and the like. The catalysts which can be utilized in the proton form or which can be prepared by supporting a catalytically active metal on the intercalated clay product of the present invention are especially useful in well-known hydrocarbon conversion processes such as catalytic cracking, hydrocracking, hydrotreating, isomerization and reforming. The metal can be incorporated within the interlamellar region of the expanded clay substrate by impregnation and/or as salts which exchange with metal ions in the clay. Upon reduction with same reducing agent such as hydrogen, the metal ions are reduced to the metal. An especially useful hydrocarbon conversion catalyst is that formed by supporting hydrogen ions, ammonium ions, an ion from Group IB to VIII of the periodic chart of mixture thereof on the intercalated clay product of the present invention. The intercalated clay product of the invention is also useful as a molecular sieve adsorbent.

The intercalated silica product of the present invention containing a catalytically active metal normally used in catalytic hydrogenation reactions such as platinum, nickel, palladium or the like can be used in a variety of hydrogenation reactions such as the hydrogenation of olefins, the hydrogenation of carbon monoxide to methanol and the hydrogenation of carbon monoxide to hydrocarbons, this latter reaction being known as the Fisher-Tropsch reaction.

As especially useful area of utility of the colloid intercalated clay of the present invention is in the conversion of hydrocarbon feedstock. In recent years, because of the depletion of worldwide petroleum feedstocks, attention has been directed to the development of alternate sources of liquid synthetic fuel and gaseous fuels from raw materials such as coal, oil shale and tar sands. Likewise, attention is also being directed to better utilization of native black oils and petroleum resids. The conversion of heavy petroleum liquids to distillate products such as gasoline normally requires catalytic processing, one of the most important of which being catalytic cracking. Molecular sieves have had an important and tremendous impact in petroleum refining in that the use of the same in various refining operations has improved conversion rates as well as product distribution. The catalytic action of molecular sieves is characterized by the following features:

(a) Organic substrates are "intersorbed" in the sieve channel system, i.e. because of the constraining pore size and the "concave" geometry of the internal zeolite surface. An incoming molecule is usually under the simultaneous action of an ensemble of surrounding catalytic sites. Consequently, substrate polarization is considerably stronger, that is, activation is easier, compared to that with conventional catalysts. Further, as a result of approximation and orientation effects operative in the channel systems, intrasorbed reactant molecules are in many cases favorably juxtaposed, with consequent decrease in the activation entropy of the reaction.

(b) Incorporation of catalytically active sites or chemically reactive species in the molecular sieve framework allows for the design and synthesis of a wide variety of specific adsorbents, catalysts and polymeric reagents.

(c) The specific geometry and dimensions of the channel system in a given molecular sieve catalyst allows for performance of molecular-shape selective processes.

Because of the unique characteristics of molecular sieves, they have been widely used in hydrocarbon conversion processes such as cracking, hydrocracking, isomerization, hydroisomerization, alkylation and dealkylation of simple aromatics. However, there are certain severe limitations with respect to the catalytic applications of molecular sieves. In particular, because of the narrow range of critical pore sizes found in such systems (approximately 3–13 Å) intrasorption and reaction of bulky or even medium-sized organic molecules is impossible. For instance, it has been demonstrated that most of the molecules present in raw coal liquids cannot penetrate into the intercrystalline pores of conventional zeolite catalysts. Furthermore, certain organic substrates, including monocyclic aromatic compounds have exhibited low intracrystalline diffusivity in zeolite media, resulting in poor recoveries and fast catalyst aging.

The colloid intercalated clay of the present invention is especially useful in the types of catalytic applications discussed above with respect to the cracking of hydrocarbons because the clay can be prepared which has a pore size which exceeds 13 Å (in both the $d_1$ and $d_3$ direction). It is expected that relatively large size organic molecules such as aromatic compounds will penetrate the pores of the clay where the desired conversion process will occur. Useful hydrocarbon conversion catalysts within the scope of the present invention are the colloid intercalated clay functionalized with ions of hydrogen and the rare earth elements including cerium, lanthanum, samarium, neodymium, gadolinium, prasecodymium and the like.

Generally speaking, the intercalated clay product of the present invention has an interlayer spacing ($d_2$) of greater than about 28 Å, depending on the clay or a spacing between the expandable layers $d_1$ of about greater than 16 Å, and a nitrogen BET surface area of about 20 to 500 m$^2$/g.

The catalysts of the instant invention and the process for preparing them will be further described below by the following illustrative embodiments which are provided for illustration and are not to be construed as limiting the invention.

COMPOSITION PREPARATION

The following illustrates the preparation of compositions of the instant invention.

EXAMPLE 1

The colloidal solution used in the example was obtained from Nyacol Products, Inc., an affiliate of The PQ Corporation and had the following properties:

| NYACOL ® COLLOIDAL CERIA (DEVELOPMENTAL) | |
| --- | --- |
| Particle Size, Millimicrons | 5–10 |
| Ceria, CeO$_2$, Wt. % | 17.0 |
| Counter Ion, Mol Acetate/mol CeO$_2$ | 6.0 |
| Specific Gravity | 1.16 |
| pH | 2.7 |
| Viscosity, Centipoise | 10 |

NYACOL ® colloidal ceria is an aqueous dispersion of cerium oxide particles carrying a slightly positive surface charge and having a high surface area to weight ratio.

To pillar the clay, 5 g of sodium bentonite (surface area about 35 m$^2$/g) was added to 29 g of the ceria colloidal suspension. The mixture was stirred at room temperature for 40 hours, the product isolated and purified by centrifugation and washing with water. The product clay were dried at 110° C. for 20 hours. X-ray analysis showed a layer separation at about 21 Å. This material had a surface area of about 150 m$^2$/g and a pore volume of about 0.14 cc/g.

The above material was then calcined at 350° C. for 1 hour in air. Analysis of the material showed that the surface area and the pore volume remained the same but the layer separation increased.

EXAMPLE 2

This material was prepared similar to Example 1 except that 50 g of cerium bentonite (surface area about 35 m$^2$/g) was added to 430 g of the ceria colloidal suspension. The mixture was stirred for 18 hours at room temperatures. The product was isolated and purified by centifugation and washing with water. The product was dried at 110° C. for 24 hours.

Figure 2:
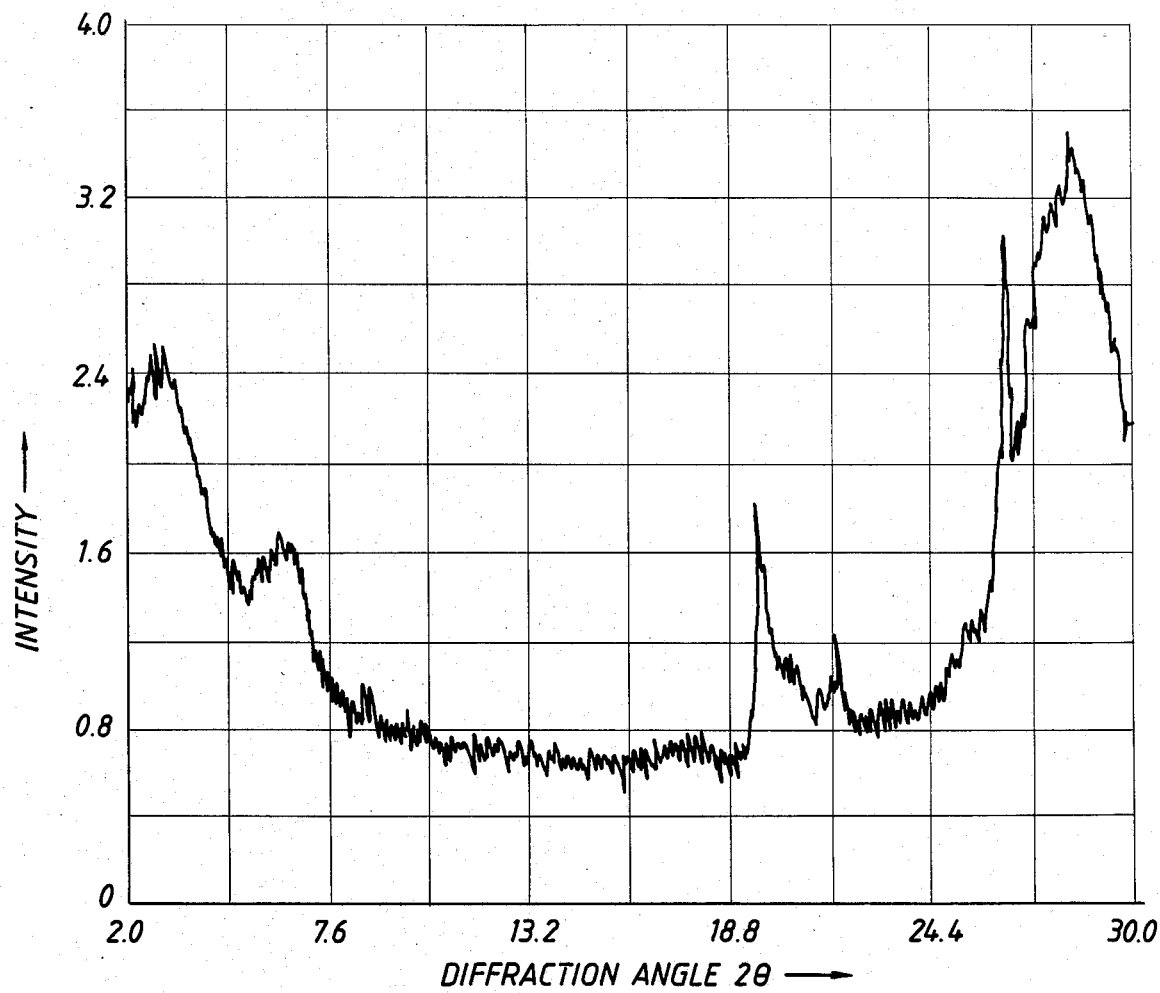
FIG. 2 is an illustration of an X-ray diffraction scan of a composition of the instant invention.

The X-ray diffractogram for the material is shown in FIG. 2. This material had a surface area of about 105 m$^2$/g and a pore volume of about 0.12 cc/g.

EXAMPLE 3

The colloidal solution used to prepare this example had the following properties:

| NYACOL ® COLLOIDAL ZIRCONIA (DEVELOPMENTAL) | |
| --- | --- |
| Particle Size, Millimicrons | 5–10 |
| Zirconia, ZrO$_2$, Weight % | 19.6 |
| Counter Ion, Mol Acetate/mol ZrO$_2$ | 0.83 |
| Specific Gravity | 1.30 |
| pH @ 25° C. | 2.7 |
| Viscosity @ 25° C., Centipoise | 10 |

NYACOL ® colloidal Zirconia is an aqueous dispersion of zirconium oxide particles carrying a slightly positive surface charge and having a high surface area to weight ratio.

To pillar the clay, 5 g of the sodium bentonite was added to 25.5 g of the zirconia suspension. The mixture was stirred at room temperature for 40 hours and the product isolated and purified by centrifugation/washing. The pillared clays were dried at 110° C. for 20 hours.

COMPOSITION UTILITY

The following example demonstrates the use of the instant composition as catalyst-support.

HEXANE HYDROISOMERIZATION

The ceria-pillared cearium bentonite of Example 2 was calcined at 350° C. for 1 hours. The material was then impregnated with tetraamine platinum (II) chloride to give a nominal 0.5% weight loading of platinum metal. The catalyst was dried at 100° C. and pelletized to 20–30 mesh particle size. The catalyst (7.5 cc, 4.05 g)

was loaded into a ⅜" ID tubular flow reactor with 60-80 mesh silicon carbide above and below the catalyst bed. The catalyst was oxidized in oxygen (500 cc/min) at 400° C. for 2 hours. The reactor was stripped with nitrogen and the catalyst reduced in hydrogen (112.5 cc/min) at 400° C. for 1 hour. The hexane isomerization reaction was then carried out with hydrogen (850 psi, 112.5 cc/min) and hexane (7.5 cc/hour). The catalyst was found to give a 30% conversion of hexane to isomerization products at about 360° C. When a comparative catalyst was prepared utilizing un-pillared cerium bentonite and run in the above reaction a higher temperature, about 385° C., was required to obtain the same degree of conversion.

We claim:

1. A clay composition comprising colloidal inorganic oxide particles intercalated between the swellable layers of said clay wherein said clay layers are separated by a distance of at least 16 angstrom.

2. A process for preparing a clay composition having inorganic oxide particles intercalated between the swellable layers of said clay which process comprises:
   a. contacting a swellable layered clay with a solution of colloidal inorganic oxide particles, said particles having net positive surface charges,
   b. separating the intercalated clay from the solution and,
   c. drying said intercalated clay.

3. The process claim 2 wherein the colloidal oxide particles are less than 100 angstroms in diameter.

4. The process of claim 3 wherein the colloidal oxide particles are less than 50 angstroms in diameter.

5. The process of claim 4 wherein the colloidal oxide particles are less than 25 angstroms in diameter.

6. The process of claim 2 wherein the dried intercalated clay is additionally calcined at a temperature ranging from about 100° C. to about 800° C.

7. The process of claim 6 wherein the temperature ranges from about 200° C. to about 600° C.

* * * * *